United States Patent [19]
Thakrar

[11] Patent Number: 6,093,463
[45] Date of Patent: **\*Jul. 25, 2000**

[54] MEDICAL DEVICES MADE FROM IMPROVED POLYMER BLENDS

[75] Inventor: Ashok R. Thakrar, San Jose, Calif.

[73] Assignee: Intella Interventional Systems, Inc., Sunnyvale, Calif.

[ * ] Notice: This patent is subject to a terminal disclaimer.

[21] Appl. No.: 09/045,483

[22] Filed: Mar. 20, 1998

Related U.S. Application Data

[63] Continuation-in-part of application No. 08/989,791, Dec. 12, 1997.

[51] Int. Cl.[7] .................................................. A61L 29/00
[52] U.S. Cl. ................. 428/36.9; 428/36.91; 428/36.92; 428/524; 604/95; 604/96; 604/101; 604/915; 604/919; 524/159
[58] Field of Search ................................ 428/35.7, 36.9, 428/36.91, 36.92; 604/95, 96, 97, 101, 102, 103, 93, 915, 919; 524/159, 288, 289, 500, 524

[56] References Cited

U.S. PATENT DOCUMENTS

| | | | |
|---|---|---|---|
| Re. 32,983 | 7/1989 | Levy | 428/36.92 |
| Re. 33,561 | 3/1991 | Levy | 428/36.92 |
| 4,490,421 | 12/1984 | Levy | 428/35 |
| 4,744,366 | 5/1988 | Jang | 128/344 |
| 4,880,904 | 11/1989 | Kinneberg et al. | 528/393 |
| 5,055,024 | 10/1991 | Jackowski et al. | 425/140 |
| 5,068,289 | 11/1991 | George et al. | 525/179 |
| 5,102,942 | 4/1992 | Machado et al. | 524/451 |
| 5,213,574 | 5/1993 | Tucker | 604/93 |
| 5,232,786 | 8/1993 | Waters et al. | 428/475.8 |
| 5,270,086 | 12/1993 | Hamlin | 428/35.2 |
| 5,281,200 | 1/1994 | Corso, Jr. et al. | 604/96 |
| 5,300,085 | 4/1994 | Yock | 606/191 |
| 5,438,988 | 8/1995 | Duan et al. | 128/640 |
| 5,500,181 | 3/1996 | Wang et al. | 264/532 |
| 5,531,690 | 7/1996 | Solar | 604/102 |
| 5,549,700 | 8/1996 | Graham et al. | 623/22 |
| 5,554,120 | 9/1996 | Chen et al. | 604/96 |
| 5,554,121 | 9/1996 | Ainsworth et al. | 604/96 |
| 5,565,523 | 10/1996 | Chen et al. | 525/176 |
| 5,567,203 | 10/1996 | Euteneuer et al. | 604/96 |
| 5,569,199 | 10/1996 | Solar | 604/96 |
| 5,569,201 | 10/1996 | Burns | 604/96 |
| 5,607,406 | 3/1997 | Hernandez et al. | 604/264 |
| 5,670,586 | 9/1997 | Ash et al. | 525/539 |
| 5,725,535 | 3/1998 | Hegde et al. | 606/108 |
| 5,849,846 | 12/1998 | Chen et al. | 525/166 |
| 5,891,114 | 4/1999 | Chien et al. | 604/282 |

FOREIGN PATENT DOCUMENTS

| | | |
|---|---|---|
| 0 171 884 A1 | 2/1986 | European Pat. Off. . |
| 0 745 395 A2 | 12/1996 | European Pat. Off. . |
| WO 95/15780 | 6/1995 | WIPO . |
| WO 95/23619 | 9/1995 | WIPO . |
| WO 96/03162A1 | 2/1996 | WIPO . |
| WO 98/54261 | 12/1998 | WIPO . |
| WO 98/54262 | 12/1998 | WIPO . |

OTHER PUBLICATIONS

"Carilon Polymers"; Shell Chemical Company; Shell Oil Company; SC:24444–96, Aug. 1996.

*Primary Examiner*—Ellis Robinson
*Assistant Examiner*—John Figueroa
*Attorney, Agent, or Firm*—Wilson Sonsini Goodrich & Rosati

[57] ABSTRACT

Disclosed are medical devices including a composition that includes an aliphatic polyketone and a thermoplastic polymer.

17 Claims, No Drawings

MEDICAL DEVICES MADE FROM IMPROVED POLYMER BLENDS

RELATED APPLICATIONS

This application is a continuation-in-part of U.S. patent application Ser. No. 08/989,791, filed Dec. 12, 1997 allowed.

BACKGROUND OF THE INVENTION

1. Field of the Invention

The present invention relates to polyketone polymers and compositions. More particularly, the invention relates to medical devices made using polyketone polymers and compositions.

2. Description of Related Art

Polymers are often materials of choice for use in medical devices, such as catheters and PTCA balloons. For example, U.S. Pat. No. 5,554,120, to Chen et al., discloses polymeric components used in forming medical devices such as catheters and balloons for dilatation catheters. U.S. Pat. No. 4,469,827 discloses polymeric compositions that can be converted into shaped articles, such as tubes, cannulae, and catheters, that are useful in the medical field. Applicant notes that all documents specifically referred to in this application, including the above mentioned patents, are incorporated by reference as if reproduced in full below.

However, polymeric materials in use today suffer from a number of disadvantages. For example, such materials may suffer from relatively high coefficients of friction, rendering intraluminal applications undesirably difficult. Additionally, several common polymeric materials are brittle, such that the frequent bending and flexing required in medical devices may cause these materials to fail prematurely. Furthermore, other common polymeric materials may not be biocompatible, making their use in medical devices unsafe and possibly illegal.

There is a need, therefore, for suitable medical devices that solve the aforementioned problems.

SUMMARY OF THE INVENTION

In an aspect, the invention relates to a medical device comprising a composition that comprises an aliphatic polyketone and a thermoplastic polymer.

DETAILED DESCRIPTION OF THE INVENTION

In one aspect, the invention relates to a medical device comprising a composition that comprises an aliphatic polyketone and a thermoplastic polymer. In another aspect, the invention relates to the medical device, wherein the composition comprises aliphatic polyketone in an amount of about 5 to about 95 weight percent, based on the total weight of the composition. In another aspect, the invention relates to the medical device, wherein the composition comprises a thermoplastic polymer in an amount of about 5 to about 95 weight percent, based on the total weight of the composition. In still another aspect, the invention relates to the medical device, wherein the thermoplastic polymer is polyamide, polyester, polyacetal, polyacrylonitrile, polyether-blockamide, polyurethane, polyethylene, or polyvinylidene fluoride. In further aspect, the invention relates to the medical device, wherein the thermoplastic polymer is polyamide.

In another aspect, the invention relates to the medical device, wherein the composition further comprises a coupling agent, a plasticizer, or a cross-linker. In still another aspect, the invention relates to the medical device, wherein the coupling agent is a zirconium or titanium coupling agent, or an epoxy modified polyolefin. In one aspect, the invention relates to the medical device, wherein the plasticizer is aromatic sulfonamides, aromatic phosphate esters, alkyl phosphate esters, alkyl esters, citrate esters, butyl benzosulfonamides, acetate, adipate, amides, azelates, epoxides, glutarates such as polyethylene, polyacetal, polyacrylonitrile glutarate, N,N-dimethyl caprylamide capramide, N,N-dimethyl oleamide, epoxidized glycol dioleate, and analogs and derivatives and mixtures thereof. In another aspect, the invention relates to the medical device, wherein the cross-linking agent is ethylene glycol dimethacrylate, triallyl isocyanurate, triallyl cyanurate, or triallyl 1,3,5-triazine-2,4,6(1 H,3 H,5 H)-trione.

In an aspect, the invention relates to the medical device, wherein the medical device is minimally invasive. In another aspect, the invention relates to such a medical device, wherein the composition comprises aliphatic polyketone in an amount of about 5 to about 95 weight percent, based on the total weight of the composition. In still another aspect, the invention relates to such a medical device, wherein the composition comprises a thermoplastic polymer in an amount of about 5 to about 95 weight percent, based on the total weight of the composition. In yet another aspect, the invention relates to such a medical device, wherein the thermoplastic polymer is polyamide, polyethylene, polyacetal, polyacrylonitrile, polyether-blockamide, polyurethane, polyester, or polyvinylidene fluoride. In another aspect, the invention relates to such a medical device, wherein the composition further comprises a coupling agent, a plasticizer, or a cross-linker.

In an aspect, the invention relates to the medical device, where the medical device comprises a percutaneous and non-intraluminal device. In another aspect, the invention relates to the medical device, wherein the medical device comprises an intraluminal tubular member. In a further aspect, the invention relates to the medical device, wherein the composition comprises aliphatic polyketone in an amount of about 5 to about 95 weight percent, based on the total weight of the composition. In another aspect, the invention relates to the medical device, wherein the composition comprises a thermoplastic polymer in an amount of about 5 to about 95 weight percent, based on the total weight of the composition. In still another aspect, the invention relates to the medical device, wherein the thermoplastic polymer is polyamide, polyethylene, polyacetal, polyacrylonitrile, polyether-blockamide, polyurethane, polyester, or polyvinylidene fluoride. In yet another aspect, the invention relates to the medical device, wherein the composition further comprises a coupling agent, a plasticizer, or a cross-linker.

In an aspect, the invention relates to the medical device, where the medical device comprises a percutaneous and non-intraluminal device. In another aspect, the invention relates to the medical device, where the medical device comprises an intravascular catheter. In still another aspect, the invention relates to the medical device, where the medical device comprises an intracoronary catheter. In yet another aspect, the invention relates to the medical device, where the medical device comprises a percutaneous device. In another aspect, the invention relates to the medical device, where the medical device comprises a non-percutaneous device.

In a further aspect, the invention relates to the medical device, where the medical device comprises an intraluminal balloon. In another aspect, the invention relates to the medical device, wherein the composition comprises aliphatic polyketone in an amount of about 5 to about 95 weight percent, based on the total weight of the composition. In still another aspect, the invention relates to the medical device, wherein the composition comprises a thermoplastic polymer in an amount of about 5 to about 95 weight percent, based on the total weight of the composition. In a further aspect, the invention relates to the medical device, wherein the thermoplastic polymer is polyamide, polyethylene, polyacetal, polyacrylonitrile, polyether-blockamide, polyurethane, polyester, or polyvinylidene fluoride. In another aspect, the invention relates to the medical device, wherein the thermoplastic polymer is polyamide. In yet another aspect, the invention relates to the medical device, wherein the composition further comprises a coupling agent, a plasticizer, or a cross-linker.

In an aspect, the invention relates to the medical device, where the medical device comprises a percutaneous device. In another aspect, the invention relates to the medical device, where the medical device comprises a non-percutaneous device. In still another aspect, the invention relates to the medical device, where the medical device comprises a single balloon. In another aspect, the invention relates to the medical device, where the medical device comprises multiple balloons. In yet another aspect, the invention relates to the medical device, wherein the balloon wall material is biaxially oriented. In still another aspect, the invention relates to the medical device, wherein the balloon is about 1.5 to 12 mm in diameter. In a further aspect, the invention relates to the medical device, wherein the balloon is capable of deploying a stent. In another aspect, the invention relates to the medical device, wherein the balloon is semi-compliant. In yet another aspect, the invention relates to the medical device, wherein the balloon wall material is perforated or is sufficiently porous to permit drug delivery through the wall material.

Applicant has previously disclosed in U.S. patent application Ser. No. 08/989,791, filed Dec. 12, 1997, compositions comprising at least one aliphatic polyketone and at least one plasticizer. Also disclosed were medical devices comprising polyketone polymer or a composition of at least one aliphatic polyketone and at least one plasticizer. Applicants have additionally discovered that compositions that comprise an aliphatic polyketone and a thermoplastic polymer can be used advantageously in medical devices, as is now discussed in more detail.

Aliphatic polyketones are a relatively newly developed class of polymers. Therefore, with the exception of the applicant's U.S. patent application Ser. No. 08/989,791, filed Dec. 12, 1997, aliphatic polyketone polymers and compositions have not been previously utilized for medical device applications.

After much research, however, the inventor has unexpectedly discovered that the properties of aliphatic polyketone polymers and compositions make them outstanding materials of construction for medical devices. This is because of desirable properties, including reasonable biocompatibility, good processability, good dimensional stability, and good tensile strength and elongation. Additionally, aliphatic polyketone polymers and compositions can be utilized in a startlingly broad range of medical devices. This is because of properties such as low coefficient of friction, excellent bondability to other medical device materials, excellent hydrolytic stability, and an easily tailorable Young's modulus. These properties allow a medical device designer considerable latitude in selecting the appropriate aliphatic polyketone polymer or composition to meet design needs. In particular, aliphatic polyketone polymers and compositions may be advantageously used in medical devices, including but not limited to, inflatable balloons and catheter shafts.

The aliphatic polyketones used in this invention are generally derived from carbon monoxide and alpha olefins. Such polyketones are generally thermoplastic in nature, and may be characterized as strong, tough, and ductile polymers. Specific aliphatic polyketone polymers are available from Shell Chemical Company (Houston, Tex.) under the trademark CARILON®. Typical properties for aliphatic polyketones may be:

| | |
|---|---|
| Specific Gravity | 1.24 |
| Tensile Strength @ yield, psi | 8,700–9,200 |
| Elongation @ yield % | 22–28 |
| @ break | 300 |
| Tensile Modulus, psi | 230,000 |
| Flexural Modulus, psi | 220,000 |
| Wear Factor | 215 × 10-10 in$^3$-min/lb-ft-hr |
| Melting Point Deg. F. | 428 |

A wide variety of thermoplastic polymers may be used in the practice of this invention. Generally speaking, most commercially available thermoplastic polymers may be used in the practice of this invention. These thermoplastic polymers usually possess properties such as good dimensional stability, low toxicity, reasonable range of stiffness and flexibility, and good compounding properties. It should be noted that the thermoplastic polymers, and the aliphatic polyketones as well, are defined herein to include copolymers, such as copolymers, terpolymers, etc., and derivatives of the thermoplastic polymers and the aliphatic polyketones, in addition to the homopolymer of the thermoplastic polymers, and the aliphatic polyketones.

While an extremely broad range of thermoplastic polymers may be used in the practice of this invention, a few thermoplastic polymers are preferrable. For example, polyamides and their derivatives may be used in the practice of this invention. Polyamides are high molecular weight polymers formed by condensation of dicarboxylic acids with diamines, condensation of ω-aminoacids, or by ring opening and polymerization of cyclic amides. Polyamides are characterized by high strength, stiffness, and hardness; high wear resistance, good slip and dry running properties, and relative non-toxicity. Additional chemistries and properties are set forth in Hans Domininghaus, *Plastics for Engineers: Materials, Properties, Applications*, 1993 (J. Haim & D. Hyatt, trans., Carl Hanser Verlag, publ.). Specific polyamides useful in the practice of this invention include Nylon-11 (available as BESNO® from Elf Atochem), Nylon 12 (available as VESTAMID® from Huls America), Nylon 6/12 (available from DSM).

Polyesters and their derivatives may also be used in the practice of this invention. Generally, speaking, polyesters useful in the practice of this invention include, but are not limited to, polycarbonates, and polyalkylene-terephthalates. Polyesters generally are characterized by low density, high strength, stiffness and hardness, and good slip and wear properties. Additional chemistries and properties are set forth in Hans Domininghaus, *Plastics for Engineers: Materials, Properties, Applications*, 1993 (J. Haim & D. Hyatt, trans., Carl Hanser Verlag, publ.). Particular polyesters useful in the practice of this invention include polyethylene terephthalate (available as TRAYTUF® from Shell), Poly(trimethylene) terephthalate (available from Shell), Polybutylene terephthalate (available as CRASTIN® from Dupont), PETG Copolyester (available from Eastman), and polyester elastomers such as HYTREL® (available from Dupont).

Polyether-blockamides and their derivatives are also useful polymers in the practice of this invention. Polyether-blockamides are thermoplastic elastomers that are generally characterized by, among other properties, good flexibility and impact resistance at low temperatures, good dynamic properties (e.g. resilience, and hysteresis), superior processing properties, and good compatibility with various fillers. Additional chemistries and properties are set forth in Elf Atochem, *Pebax: Basis of Performance* (*Polyether Block Amides*), (available from Elf Atochem). Examples of such polyether-blockamides are available as PEBAX® from Elf Atochem.

Polyurethane and its derivatives are also useful in the practice of this invention. Polyurethanes may be obtained by a variety of chemistries. One of the most common is the polycondensation of isocyanate monomers with alcohols or other materials containing reactive oxygen moieties (eg. polyesters), although other chemistries may also be used. Polyurethanes are characterized by rapid curing, low shrinkage, good adhesion, high chemical resistance, good flexibility, and safe handling of the cured polymer. Additional chemistries and properties are set forth in Hans Domininghaus, *Plastics for Engineers: Materials, Properties, Applications,* 1993 (J. Haim & D. Hyatt, trans., Carl Hanser Verlag, publ.). Particular polyurethanes useful in the practice of this invention include TECOFLEX® EG85A available from TherMedics, Inc.), PU/PC blends (such as TEXIN® available from Bayer), and PELLE-THANE® 2363 available from Dow Plastics.

Polyolefins and their derivatives may also be used in the practice of this invention. Polyolefins can be synthesized using a broad variety of chemistries, but are most often made using a catalyzed free radical polymerization reaction. Generally speaking, polyolefins are characterized by relatively low density, high toughness, high chemical resistance, and good processability and machinability. Additional chemistries and properties are set forth in Hans Domininghaus, *Plastics for Engineers: Materials, Properties, Applications,* 1993 (J. Haim & D. Hyatt, trans., Carl Hanser Verlag, publ.). Polyolefins that are preferrable in the practice of this invention include polyethylenes, polypropylenes, polyolefin copolymers, polyolefin terpolymers, polybutylene, polypentylene, and polyolefin blends. Specific examples of polyolefins useful in the practice of this invention include polyethylene (available as AFFINITY® PL .1850 from Dow Chemical), terpolymer polyolefin blends (available as SLX 9090 from Exxon), and polypropylene (available as PDC 1188 from Montel).

Polyacrylonitrile and its derivatives may also be used in the practice of this invention. Polyacrylonitrile can be synthesized using a broad variety of chemistries, but are most often made using a catalyzed free radical polymerization reaction. Generally speaking, polyacrylonitrile is characterized by relatively high strength, high modulus of elasticity, and high impact strength. Additional chemistries and properties are set forth in Hans Domininghaus, *Plastics for Engineers: Materials, Properties, Applications,* 1993 (J. Haim & D. Hyatt, trans., Carl Hanser Verlag, publ.). Polyacrylonitriles that are useful in the practice of this invention include copolymers that include polyacrylonitrile, such as poly(styrene/acrylonitrile), and poly(acrylonitrile-butadiene-styrene). Specific examples of polyacrylonitrile useful in the practice of this invention include DOLAN® available from Hoechst.

Polyacetal and its derivatives may also be used in the practice of this invention. Polyacetals are polymerized from formaldehyde and are technically called polyoxymethlyenes. Polyacetals are characterized by their strength, stiffness, and hardness, and are stable over a wide range of physical conditions. Additional information regarding chemistries and properties may be found in in *Modern Plastics Encyclopedia,* B-69 (1997). Specific examples of polyacetals useful in the practice of this invention include DELRIN® (available from E. I. Du Pont), ULTRAFORM® (available from BASF Corporation's Ultraform Co.), and CELCON® (available from Hoechst-Celanese).

Polyvinylidene fluoride and its derivatives can also be used in the practice of this invention. Polyvinylidene fluoride can be synthesized in a variety of ways; the most preferrable way being free radical polymerization of vinylidene fluoride monomer. Polyvinylidene fluoride is generally characterized by high mechanical strength, stiffness, and toughness, good toughness, and good chemical resistance. Additional chemistries and properties are set forth in Hans Domininghaus, *Plastics for Engineers: Materials, Properties, Applications,* 1993 (J. Haim & D. Hyatt, trans., Carl Hanser Verlag, publ.). Specific polyvinylidene fluorides useful in the practice of this invention include 1015/0078 available from Solvay.

Other ingredients and materials besides aliphatic polyketones and thermoplastic polymers may be used in the compositions according to the invention. For example, additives such as processing aids, including stearates, or low molecular weight waxes; antioxidants; colorants; or other conventional additives may be added. These additives may be used separately or in combinations, according to the desired final properties of the inventive compositions. The use of such additives in medical device compositions, such as the inventive compositions, is customary, is well understood by one of skill in the art, and is within the scope of the invention.

Three types of additives that are preferrable are coupling agents, plasticizers, and cross-linkers. Coupling agents useful in the practice of this invention can be of a wide variety of types. Generally speaking, the coupling agents useful in the practice of the invention share the characteristics that they affect the interfacial properties of the aliphatic polyketones and thermoplastic polymers of the inventive compositions in a way that enhances the physical properties of the medical device that comprises the compositions. Preferrable coupling agents include titanium and/or zirconium coupling agents, and polymeric coupling agents.

Titanium and/or zirconium coupling agents are generally tetrafunctional organo-metallic compounds whose central metal tetravalency is conducive to electron sharing. This property makes them good candidates for modifying the interfacial properties of the inventive compositions comprising aliphatic polyketones and thermoplastic polymers. Titanium coupling agents come in a variety of forms, including monoalkoxy, chelates, coordinates, quat salts, neoalkoxy, and cycloheteroatom. Zirconium coupling agents are also available in a variety of forms, including neoalkoxy zirconates. Such coupling agents may be obtained from Kenrich Petrochemicals (140 East 22nd Street, Bayonne N.J.) under the trademark KEN-REACT®. Additional information regarding the properties of titanium and zirconium coupling agents, including information regarding use and incorporation, may be found in Salvatore J. Monte, *Ken-React Reference Manual* (1993) (Kenrich Petrochemicals, publ.).

Titanium and/or zirconium coupling agents may be used in an amount effective to optimize the physical properties of the medical device that comprises the composition comprising the coupling agents. More preferably, the titanium or zirconium coupling agents may be present in an amount of 0.1 to 5.0 weight percent based on the total weight of the composition. Most preferrable is 1% weight percent of the coupling agent.

Polymeric coupling agents are widely used to modify the interfacial properties of polymer compositions. This wide use, and the resulting commercial availability of these coupling agents, makes them good candidates for use as coupling agents in the inventive compositions comprising aliphatic polyketones and thermoplastic polymers.

Generally, the polymeric coupling agents according to the invention can be selected using a few rules. First, the polymeric coupling agents may be a polymer that is made up of chemically distinct sections, some of which are miscible with the aliphatic polyketone, and some of which are miscible with the thermoplastic polymer. Of course, when additional polymers are present in the composition, the polymeric coupling agent or agents may be miscible with them as well. Additionally, the polymeric coupling agent is more effective when its sections are of higher molecular weight than the corresponding components of the composition. Finally, block copolymers and graft copolymers are the most widely used polymeric coupling agents, and therefore are more likely to be readily available, although other types of polymeric coupling agents may be used as appropriate. Additional information regarding polymeric coupling agents, including use and incorporation, may be found in Sudhin Dafta and David J. Lohse, *Polymeric Compatibilizers: Uses and Benefits in Polymer Blends* (1996) (Carl Hanser Verlag, publ.).

A preferable class of polymeric coupling agents includes epoxy modified polyolefins, most preferrably ethylene-n-butyl acrylate-maleic anhydride terpolymers and ethylene-ethyl acrylate-maleic anhydride terpolymers. Specific examples of polymeric coupling agents useful in the practice of this invention include POLYBOND® (available from Uniroyal Chemical), and LOTADER® MAH (available from Elf AtoChem). Polymeric coupling agents, when used, may be present in an amount effective to optimize the physical properties of the medical device that comprises the composition comprising the coupling agents. More preferably, the polymeric coupling agents may be present in an amount of 0.1 to 5 weight percent based on the total weight of the composition. Most preferable is 1% by weight of the coupling agent, based on the total weight of the composition.

Additionally, the properties of the compositions according to the invention may be improved by using plasticizers. Plasticizers are materials that may be added to polymeric materials primarily to improve flexibility. In addition, plasticizers may reduce melt viscosity and lower the glass transition temperature of the polymeric materials. By varying the level of plasticizer, it may be possible to vary the final properties of the plasticized polymeric material. Plasticizers usable with the compositions according to the present invention preferably are polar, although nonpolar plasticizers may also be used.

Examples of plasticizers include, but are not limited to aromatic sulfonamides, aromatic phosphate esters, alkyl phosphate esters, alkyl esters, citrate esters, butyl benzosulfonamides, acetate, adipate, amides, azelates, epoxides, glutarates such as polyester glutarate, N,N-dimethyl caprylamide capramide, N,N-dimethyl oleamide, epoxidized glycol dioleate, and analogs and derivatives and mixtures thereof.

The plasticizers used in this invention are known to one of skill in the art and are readily available from conventional suppliers. For example, citrate esters are derived from citric acids, generally have benign toxicology, and are available as CITROFLEX® from Morflex, Inc (Greensboro, N.C.). Butyl benzosulfamides generally are light yellow liquids, having a pleasant odor, and are available as PLASTHALL® from the C. P. Hall Company (Chicago, Ill.). Further discussion of suitable plasticizers can be found in *Modern Plastics Encyclopedia*, C-99-108 (1997).

Preparing the compositions according to the invention can be accomplished in a variety of ways. One of the most straightforward is compounding of the various ingredients in the composition. Compounding according to the invention can be done according to methods known in the art, such as extrusion. Such methods are generally described in *Two Phase Polymer Systems*, 69–91 (1991)(L. a. Utracki, ed.). In addition, other ways of preparing the recited composition might be used, including preparing polymeric alloys, and other methods known to one of skill in the art.

Excessive use of plasticizer in the compositions according to the invention should be avoided because it may lead to blooming or leaching of the plasticizer and/or phase separation. In a preferable embodiment, plasticizer may be present in an amount effective to optimize the physical properties of the medical device that comprises the composition comprising the plasticizer. More preferable amounts of plasticizers incorporated into the compositions according to the invention range from about 0.01 to about 20 weight percent on the total composition weight, most preferably from about 5 to about 20 weight percent on the total composition weight.

Furthermore, cross-linkers may be used in the practice of a preferrable embodiment of this invention. Crosslinkers function generally to link together polymer chains into a three dimension structure. Crosslinkers can be divided into at least two groups: internal and external. Both external and internal crosslinkers can be used in the practice of this invention. Internal crosslinkers are monomers or oligomers that are structurally incorporated into the polymeric backbone of the polymers to be crosslinked. Internal crosslinkers may be existing functionalities in the polymer (such as double bonds in unsaturated polyolefins), or may be functionalities added specifically for the purpose of creating crosslinking capability. External crosslinkers, by comparison, are induced to link already substantially polymerized polymers, and are mixed together with the polymers to be crosslinked. Preferable external crosslinkers include multifunctional monomers or oligomers. Especially preferable external crosslinkers include di- or tri-functional monomers. Most preferable crosslinkers include ethylene glycol dimethacrylate, triallyl isocyanurate (available as PERKALINK® 301 from Akzo Nobel), triallyl cyanurate (available as PERKALINK® 300 from Akzo Nobel), or triallyl 1,3,5-triazine-2,4,6(1 H,3 H,5 H)-trione (available from SAF, Inc.).

The composition of the medical device according to the invention may be cross linked before or after it had been formed. In a preferrable embodiment, the medical device is first formed, and then crosslinked. While the way of crosslinking the inventive medical devices will depend primarily upon the crosslinkers used, a preferable way of crosslinking the inventive recited compositions is by gamma or electron beam radiation techniques. Another preferable way of crosslinking the inventive recited compositions is by exposure to heat. The degree of crosslinking can be controlled by adjusting the ratio of crosslinker added to the amount of other material present in the composition, or by adjusting the amount of radiation or heat supplied to crosslink the composition. Generally, in a preferrable embodiment, the amount of crosslinker may be present in an amount effective to optimize the physical properties of the medical device that comprises the composition comprising the crosslinker. In a more preferrable embodiment, the crosslinker may be present in an amount of about 0.1 to about 5 weight percent on the total composition weight, most preferably about 1 weight percent on the total composition weight.

The ingredient concentrations of the recited inventive compositions may vary from embodiment to embodiment. Preferably, the compositions making up the inventive medical device will have from about 1 to about 99 weight percent aliphatic polyketone, more preferably about 5 to about 95 weight percent aliphatic polyketone, based on the total composition weight. Additionally, preferably the compositions making up the inventive medical device will have from about 1 to about 99 weight percent thermoplastic polymer, more preferably about 5 to about 95 weight percent thermoplastic polymer, based on the total composition weight. Miscellaneous other additives or materials included in the inventive compositions may be included in a preferrable amount of about zero to about five weight percent on the total composition weight, more preferably from about 0.01 to about 5 weight percent on the total composition weight. Preferably, the total amount of plasticizers, additives and other materials is less than about 20 weight percent of based on the total composition weight.

Conventional methods for making polymeric medical devices can be easily adapted by one of skill in the art to making medical devices from the compositions of the present invention. This is because the compositions according to the invention can be worked using techniques that are conventional in the polymer art. In particular, catheter balloons having oriented wall materials of the inventive composition can be made according to the general teachings of Levy, U.S. Pat. No. Re 33,561, and Jackowski et al, U.S. Pat. No. 5,055,024.

The inventive compositions can be used to make a variety of medical devices, as noted above. Generally speaking, polyketone polymers and Acompositions can be used with existing medical device architectures, or can be used to create entirely new devices based on the superior properties of the inventive compositions. For example, the inventive compositions can be used in conventional intraluminal catheters shafts, replacing polyethylene or polyurethane. Alternatively, the inventive compositions may be used to create surgical tools and implements. In a proper formulation, the inventive compositions may even be able to be used in long-term implant devices, such as stents, pacemakers, or bone or cartilage replacements. In a preferrable embodiment, the inventive compositions can be used to create balloon catheters having balloons with improved properties. More preferably, such balloon catheters according to the invention are semi-compliant.

An example of this is illustrated by the combination of known multiple balloon catheter architectures with the inventive compositions. In Jang, U.S. Pat. No. 4,744,366, a multiple balloon catheter architecture is disclosed. The term multiple balloon is used herein to mean more than one balloon. The materials of construction disclosed for use as catheter balloon materials are polyvinyl chloride, polyester, and polyethylene. These materials can be advantageously substituted with the inventive compositions. Such a substitution may result in balloons with lower coefficients of friction and improved folding properties, thus enhancing the balloon's and overall catheter system's performance.

Other known medical device architectures may be adapted for use with polyketone polymers and compositions according to the invention. For example Corso, Jr. et al. (U.S. Pat. No. 5,281,200), Yock (U.S. Pat. No. 5,300,085), Solar (U.S. Pat. No. 5,531,690), Euteneuer et al. (U.S. Pat. No. 5,567,203), Solar (U.S. Pat. No. 5,569,199), Burns (U.S. Pat. No. 5,569,201), and Hernandez et al. (U.S. Pat. No. 5,607,406) all disclose structures that may be adapted for use with the present invention, using polymer techniques well known in the art.

EXAMPLES

Physical properties of the medical device compositions including aliphatic polyketones and thermoplastic polymers according to the invention were compared with conventional medical device materials, particularly polyester and plasticized nylon. The tests were performed on both standard test pieces and sample balloons according to the following procedures.

The tensile property of the balloons were measured using a Chatilon tensile tester model TCD 200. In this procedure, one end of the cylindrical part of the balloon was attached to the lower jaw and the other end was attached to the upper jaw which was then attached to a load cell. The distance between the two jaws was measured and the sample was pulled at 0.5 inch/minute until torn. Total deflection and the force gauge reading were recorded. The tensile property of the tested balloon and its elongation were calculated as follows:

Tensile Strength=Force/(Double Wall thickness/2)* PI *Diameter of the Balloon

% Elongation={(Final length−Original length)/Original length}*100

The coefficient of friction was measured for catheter shafts by wrapping the sample catheter shaft a full 360 degrees around a pulley made out of polyacetal material. A known tension (T1) was placed at the one end of the catheter shaft and the catheter shaft was pulled from the other end. The resulting dynamic tension (T2) was measured using a Chatilon tensile tester. The coefficient of friction was calculated using the following equation:

$f=\beta \ln(T2/T1)$ where f=coefficient of friction
β=angle of tension T1 and T2
T1=known tension at the bottom of the shaft
T2=dynamic tension Stiffness of the catheter shafts were tested using a three point bending method where an approximately 2 inch long piece of a shaft was deflected on a supported beam under the action of a centrally located point load. The ratio of deflection to sample length was less than or equal to 0.06. Using the following equation the stiffness and modulus of elasticity were calculated.

$\delta=(F.L^3)/(48.EI)=(F.L^3)/(48.Sb)$ Hence, $Sb=EI=(F.L^3)/(48.\delta)$

δ  = deflection, mm
Sb = bending stiffness of the sample in N-mm$^2$
F  = force applied, Newtons
L  = length, mm
E  = modulus of elasticity, N/mm$^2$
I  = moment of inertia, Ix = Iy of the beam X section about the neutral axis, mm$^4$ Balloon burst tests were carried out using a Crescent Design's Hydraulic Burst -Leak Tester Model 100, according to the manufacturer's instructions.

Example 1

A molding composition was prepared by compounding 30 weight percent of aliphatic polyketone R-1000 (available from Shell Chemical Company) with 70 weight percent PEBAX® 6333 (available from Elf Atochem). The composition was compounded on a 27 mm Leistritz twin screw extruder, using a conventional homogenizing screw design. The screw speed was 345 RPM and the melt temperature was 440 Deg. F. The extruded blend was pelletized and collected. This blend was then re-extruded into a 0.019/0.038"ID/OD tube using a 25 mm single screw extruder. The barrel temperature ranged from 420 Deg. F. to 480 Deg. F. from feeding zone to the die head respectively. Test pieces, including 2.5 mm diameter balloons were prepared using conventional techniques. The test pieces were then tested, with the results as shown in Tables 1 and 2.

Example 2

A molding composition was prepared by compounding 10 weight percent of aliphatic polyketone R-1000 (available from Shell Chemical Co.) with 17 weight percent butyl benzosulfonamide (available as PLASTHALL® from C. P. Hall Company), and 73 weight percent nylon 12 (available as L2106F from Huls America). The composition was compounded on a 27 mm Leistritz twin screw extruder, using a conventional homogenizing screw design. The screw speed was 345 RPM and the melt temperature was 470 Deg. F. The extruded blend was pelletized and collected. This blend was then re-extruded into a 0.019/0.038"ID/OD tube using a 25 mm single screw extruder. The barrel temperature ranged from 450 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

Example 3

A molding composition was prepared by compounding 75 weight percent of aliphatic polyketone R-1000 (available from Shell Chemical Co.) with 25 weight percent nylon 12 (available as L2106F from Huls America). The composition was compounded on a 27 mm Leistritz twin screw extruder, using a conventional homogenizing screw design. The screw speed was 345 RPM and the melt temperature was 470 Deg. F. The extruded blend was pelletized and collected. This blend was then re-extruded into a 0.019/0.038"ID/OD tube using a 25 mm single screw extruder. The barrel temperature ranged from 450 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

Comparative Example 4

Polyketone Resin (CARILON® R-10000, available from Shell Chemical, Akron, Ohio) was extruded into a 0.019/0.038"ID/OD tube using a 25 mm single screw extruder. The barrel temperature ranged from 450 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

Comparative Example 5

Polyester Resin (TRAYTUF® available from Shell Chemical, Akron, Ohio) was extruded into a 0.019/0.038"ID/OD tube using a 25 mm single screw extruder. The barrel temperature ranged from 520 Deg. F. to 560 Deg. F. from feeding zone to the die head respectively. Test pieces, including 2.5 mm diameter balloons were prepared using conventional techniques. The test pieces were then tested, with the results as shown in Tables 1 and 2.

Comparative Example 6

Plasticized Polyamide resin (VESTAMID® L-2124, available from Huls America) was extruded into a 0.019/0.038"ID/OD tube using a 25 mm single screw extruder. The barrel temperature ranged from 420 Deg. F. to 460 Deg. F. from feeding zone to the die head respectively. Test pieces, including 2.5 mm diameter balloons were prepared using conventional techniques. The test pieces were then tested, with the results as shown in Tables 1 and 2.

Comparative Example 7

A molding composition of 90 weight percent of aliphatic polyketone R-1000 (available from Shell Chemical Co.) was prepared by plasticizing with 10 weight percent of Triethyl Citrate (available from Moreflex as CITROFELX®). The composition was compounded on a 27 mm Leistritz twin screw extruder, using a conventional homogenizing screw design. The screw speed was 345 RPM and the melt temperature was 250 C. The extruded blend was pelletized and collected. This blend was then re-extruded into a 0.019/0.038"ID/OD tube using a 25 mm single screw extruder. The barrel temperature ranged from 440 Deg. F. to 490 Deg. F. from feeding zone to the die head respectively. Test pieces, including 2.5 mm diameter balloons were prepared using conventional techniques. The test pieces were then tested, with the results as shown in Tables 1 and 2.

Example 8

A molding composition is prepared by compounding 30 weight percent of aliphatic polyketone R-1000 (available from Shell Chemical Co.) with 70 weight percent nylon 12 (available as L2106F from Huls America). The composition is compounded on a 27 mm Leistritz twin screw extruder, using a conventional homogenizing screw design. The screw speed is 345 RPM and the melt temperature was 470 Deg. F. The extruded blend is pelletized and collected. This blend is then re-extruded into a 0.019/0.038"ID/OD tube using a 25 mm single screw extruder. The barrel temperature ranges from 450 Deg. F. to 490 Deg. F. from feeding zone to the die head respectively. Test pieces, including 2.5 mm diameter balloons are prepared using conventional techniques.

Example 9

A molding composition was prepared by compounding 75 weight percent of aliphatic polyketone R-1000 (available from Shell Chemical Co.) with 25 weight percent PEBAX® 6333 (available from Elf Atochem). The composition is compounded on a 27 mm Leistritz twin screw extruder, using a conventional homogenizing screw design. The screw speed is 345 RPM and the melt temperature was 470 Deg. F. The extruded blend is pelletized and collected. This blend is then re-extruded into a 0.019/0.038"ID/OD tube using a 25 mm single screw extruder. The barrel temperature ranges from 450 Deg. F. to 490 Deg. F. from feeding zone to the die head respectively. Test pieces, including 2.5 mm diameter balloons are prepared using conventional techniques.

Example 10

A molding composition was prepared by compounding 10 weight percent of aliphatic polyketone R-1000 (available from Shell Chemical Co.) with 10 weight percent butyl benzosulfonamide (available as PLASTHALL® from C. P. Hall Company), and 80 weight percent nylon 12 (available as L2106F from Huls America). The composition is compounded on a 27 mm Leistritz twin screw extruder, using a conventional homogenizing screw design. The screw speed is 345 RPM and the melt temperature was 470 Deg. F. The extruded blend is pelletized and collected. This blend is then re-extruded into a 0.019/0.038"ID/OD tube using a 25 mm single screw extruder. The barrel temperature ranges from 450 Deg. F. to 490 Deg. F. from feeding zone to the die head respectively. Test pieces, including 2.5 mm diameter balloons are prepared using conventional techniques.

Example 11

A molding composition was prepared by compounding 10 weight percent of aliphatic polyketone R-1000 (available from Shell Chemical Co.) with 9 weight percent butyl benzosulfonamide (available as PLASTHALL® from C. P. Hall Company), 80 weight percent nylon 12 (available as L2106F from Huls America), and 1 weight percent triallyl isocyanurate (available as PERKALINK® from Akzo Nobel). The composition is compounded on a 27 mm Leistritz twin screw extruder, using a conventional homogenizing screw design. The screw speed is 345 RPM and the melt temperature was 470 Deg. F. The extruded blend is pelletized and collected. This blend is then re-extruded into a 0.019/0.038"ID/OD tube using a 25 mm single screw extruder. The barrel temperature ranges from 450 Deg. F. to 490 Deg. F. from feeding zone to the die head respectively. Test pieces, including 2.5 mm diameter balloons are prepared using conventional techniques. The test pieces are then crosslinked using electron beam radiation.

Example 12

The molding composition of Example 3 is extruded into a flexible elongate tubular member having a 3 French diameter and a length of 150 centimeters. The structure of the tubular member is generally disclosed in U.S. Pat. No. 5,725,535 to Hegde et al. The tubular member is then incorporated into a multiple balloon stent delivery catheter, which has the structure as disclosed in U.S. Pat. No. 5,725,535. The catheter is used as is disclosed in U.S. Pat. No. 5,725,535 to deliver a stent in a coronary vessel.

Example 13

The molding composition of Example 3 is extruded into a flexible balloon having a two millimeter diameter. The structure of the balloon is generally disclosed in U.S. Pat. No. 5,725,535 to Hegde et al. The balloon is then incorporated into a multiple balloon stent delivery catheter, which has the structure as disclosed in U.S. Pat. No. 5,725,535. The catheter is used as is disclosed in U.S. Pat. No. 5,725,535 to deliver a stent in a coronary vessel via inflation of the balloon.

TABLE 1

| Example Numbers | Coefficient of Friction | | Balloons Properties | | Burst Pres. |
|---|---|---|---|---|---|
| | IN AIR | IN WATER | Tensile psi | Elongation % | atm. |
| 1 | 0.1214 | 0.1160 | 13128 | 188 | 10 |
| 2 | 0.1390 | 0.1011 | 14391 | 147 | 24 |
| 3 | 0.1045 | 0.1028 | 37220 | 74 | 22 |
| 4 (Comparative) | 0.100 | 0.084 | 24870 | 72 | 24 |
| 5 (Comparative) | 0.090 | 0.073 | 28000 | 50 | 27 |
| 6 (Comparative) | 0.160 | 0.110 | 17900 | 67 | 17 |
| 7 (Comparative) | 0.116 | 0.107 | 19200 | 59 | 18 |

TABLE 2

| Example Numbers | Bending Stiffness N-mm2 | Young's Modulus of Elasticity N/mm2 |
|---|---|---|
| 1 | 15.0 | 2041 |
| 2 | 17.0 | 1499 |
| 3 | 26.0 | 1967 |
| 4 (Comparative) | 23.6 | 1685 |
| 5 (Comparative) | 111.0 | 8455 |
| 6 (Comparative) | 9.9 | 1846 |
| 7 (Comparative) | 18.2 | 1846 |

It will be apparent to those skilled in the art that various modifications and variations can be made in the devices and compositions of the present invention without departing from the spirit or scope of the invention. Thus, it is intended that the present invention cover the modifications and variations of this invention provided that they come within the scope of the appended claims and their equivalents.

What is claimed is:

1. An intraluminal balloon that comprises a composition comprising (a) at least one aliphatic polyketone; and
   (b) a thermoplastic polymer;
   wherein the at least one aliphatic polyketone is derived from monomers consisting of carbon monoxide and alpha olefins.

2. The intraluminal balloon of claim 1, wherein the at least one aliphatic polyketone is present in an amount of about 5 to about 95 weight percent, based on the total weight of the composition.

3. The intraluminal balloon of claim 1, wherein the thermoplastic polymer is present in an amount of about 5 to about 95 weight percent, based on the total weight of the composition.

4. The intraluminal balloon of claim 1, wherein the thermoplastic polymer comprises polyamide, polyester, polyether-blockamide, polyurethane, polyethylene, polyacetal, polyacrylonitrile, or polyvinylidene fluoride.

5. The intraluminal balloon of claim 1, wherein the thermoplastic polymer comprises polyamide.

6. The intraluminal balloon of claim 1, further comprising a plasticizer.

7. An intraluminal balloon that comprises a composition comprising (a) at least one aliphatic polyketone;

(b) a coupling agent or a cross-linker; and further comprising (c) a thermoplastic polymer;

wherein the at least one aliphatic polyketone is derived from monomers consisting of carbon monoxide and alpha olefins.

8. The intraluminal balloon of claim 7, wherein the coupling agent comprises a zirconium or titanium coupling agent, or an epoxy modified polyolefin.

9. The intraluminal balloon of claim 7 further comprising a plasticizer, wherein the plasticizer comprises aromatic sulfonamides, aromatic phosphate esters, alkyl phosphate esters, alkyl esters, citrate esters, butyl benzosulfonamides, acetate, adipate, amides, azelates, epoxides, glutarates such as polyester glutarate, N,N-dimethyl caprylamide capramide, N,N-dimethyl oleamide, epoxidized glycol dioleate, analogs of any of the above, derivatives of any of the above or mixtures thereof.

10. The intraluminal balloon of claim 7, wherein the cross-linking agent comprises ethylene glycol dimethacrylate, triallyl isocyanurate, triallyl cyanurate, or triallyl 1,3,5-triazine-2,4,6(1 H,3 H,5 H)-trione.

11. The intraluminal balloon of claim 7 having a wall comprising a balloon wall material, wherein the balloon wall material is biaxially oriented.

12. The intraluminal balloon of claim 7, wherein the balloon is about 1.5 to 12 mm in diameter.

13. The intraluminal balloon of claim 7, wherein the balloon is capable of deploying a stent.

14. The intraluminal balloon of claim 7, wherein the balloon is semi-compliant.

15. The intraluminal balloon of claim 1 having a wall comprising a balloon wall material, wherein the balloon wall material is perforated or is sufficiently porous to permit drug delivery through the wall material.

16. An intraluminal balloon formed by a process comprising:

combining at least one aliphatic polyketone and a thermoplastic polymer with an additive comprising a coupling agent, a plasticizer, or a cross-linker; and forming the combination of the at least one aliphatic polyketone and the substance into an intraluminal balloon;

wherein the at least one aliphatic polyketone is derived from monomers consisting of carbon monoxide and alpha olefins.

17. An intraluminal balloon formed by a process comprising:

combining at least one aliphatic polyketone with a thermoplastic polymer; and forming the combination of the at least one aliphatic polyketone with a thermoplastic polymer into an intraluminal balloon;

wherein the at least one aliphatic polyketone is derived from monomers consisting of carbon monoxide and alpha olefins.

* * * * *